United States Patent
Kaneda et al.

US006410809B1

(10) Patent No.: US 6,410,809 B1
(45) Date of Patent: Jun. 25, 2002

(54) CYCLOHEXANEDIMETHANOL COMPOUND AND PROCESS OF PRODUCING PRODUCTIVE INTERMEDIATES THEREFOR

(75) Inventors: Masato Kaneda; Yoshihiro Honda, both of Oita (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/647,063

(22) PCT Filed: Jul. 13, 2000

(86) PCT No.: PCT/JP00/04694
§ 371 (c)(1),
(2), (4) Date: Sep. 26, 2000

(87) PCT Pub. No.: WO01/05736
PCT Pub. Date: Jan. 25, 2001

(30) Foreign Application Priority Data

Jul. 14, 1999 (JP) ............................................. 11-199977

(51) Int. Cl.⁷ .............................................. C07C 31/27
(52) U.S. Cl. ....................................... 568/883; 568/446
(58) Field of Search ................................. 568/823, 831, 568/446

(56) References Cited

U.S. PATENT DOCUMENTS

| | | | | |
|---|---|---|---|---|
| 2,564,405 A | * | 8/1951 | Morris | |
| 2,999,866 A | * | 9/1961 | Starcher | |
| 3,067,244 A | * | 12/1962 | Robinson | |
| 3,110,688 A | * | 11/1963 | Campbell | |
| 3,446,855 A | * | 5/1969 | Jackson | |
| 3,812,059 A | * | 5/1974 | Rijke | |
| 4,666,630 A | * | 5/1987 | Wiegers | |
| 4,704,477 A | | 11/1987 | Gebauer et al. | |

FOREIGN PATENT DOCUMENTS

| | | |
|---|---|---|
| JP | 49-11684 | 3/1974 |
| JP | 6-305984 | 11/1994 |
| JP | 9-262479 | 10/1997 |
| JP | 10-45702 | 2/1998 |
| JP | 10-306056 | 11/1998 |
| JP | 11-35665 | 2/1999 |
| JP | 11-80305 | 3/1999 |
| JP | 11-189637 | 7/1999 |

* cited by examiner

*Primary Examiner*—Michael L. Shippen
(74) *Attorney, Agent, or Firm*—Sughrue Mion, PLLC

(57) ABSTRACT

A process of producing a 1,1-cyclohexanedimethanol compound having a substituent group at the 2-position in which the step of producing a 1-hydroxymethyl-3-cyclohexene-1-carbaldehyde compound by Diels-Alder reaction of a β-substituted-α,β-unsaturated aldehyde and a chain conjugated diene compound using an anhydrous tin (IV) halide catalyst is essential and a process of producing productive intermediates therefor. 1,1-Cyclohexanedimethanol compounds having a substituent group at least at the 2-position thereof obtained by the present invention are useful as a raw material for polyesters, unsaturated polyesters, alkyds, polyurethanes, epoxy resins, acrylic resins, etc. and as raw materials for functional organic compounds.

14 Claims, No Drawings

CYCLOHEXANEDIMETHANOL COMPOUND AND PROCESS OF PRODUCING PRODUCTIVE INTERMEDIATES THEREFOR

TECHNICAL FIELD

The present invention relates to a 1,1-cyclohexanedimethanol compound and a process for producing productive intermediates therefor. More particularly, the present invention relates to a process of producing a 1,1-cyclohexanedimethanol compound having a substituent group at least at the 2-position thereof, useful as a raw material for polyesters, unsaturated polyesters, alkyds, polyurethanes, epoxy resins, acrylic resins, etc., or as a raw material for functional organic compounds, to a process of producing a 3-cyclohexene-1-carbaldehyde compound having a substituent group at least at the 6-position thereof, which is a productive intermediate for the 1,1-cyclohexanedimethanol compound, to a process of producing a 1-hydroxymethyl-3-cyclohexene-1-carbaldehyde compound having a substituent group at least at the 6-position thereof, and to novel 1-hydroxymethyl-6-methyl-3-cyclohexene-1-carbaldehyde.

BACKGROUND ART 1,1-cyclohexanedimethanol compounds having a substituent group at the 2-position thereof are compounds useful as a raw material for resins. JP-A-11-35665 discloses a polyester having high heat resistance, transparency and resistance to hydrolysis derived from a 1,1-cyclohexanedimethanol compound having a substituent group at the 2-position thereof as a starting material. Also, JP-A-11-80305 and JP-A-11-189637 disclose polyurethanes having increased heat resistance derived from the above compound as a starting material of the polyurethane.

As the process of producing the 1,1-cyclohexanedimethanol compound having a substituent group at the 2-position thereof, there is a report by Shortridge, et al. on, for example, 2-methyl-1,1-cyclohexanedimethanol (R. W. Shortridge, et al., J. Am. Chem. Soc., 70, 946 (1948)). According to this process, 6-methyl-3-cyclohexene-1-carbaldehyde obtained by thermal Diels-Alder reaction between butadiene and crotonaldehyde is subjected to Cannizzaro reaction with formaldehyde in the presence of an alkali to synthesize 6-methyl-3-cyclohexene-1,1-dimethanol, followed by hydrogenating the double bond thereof to produce 2-methyl-1,1-cyclohexanedimethanol. However, this process has the problems that the thermal Diels-Alder reaction is low in yield, that the reaction has the danger of runaway or the like so that it is difficult to control it, and that formic acid salts, etc. by-produced in the Cannizzaro reaction in the second stage will deteriorate the quality of product so that a high load is imposed on the system for the separation and purification in order to remove the byproducts. Generation of byproducts will lead to an increase in the units of alkali and formaldehyde and therefore, the process is unsatisfactory for industrial application.

The Diels-Alder reaction between a β-substituted-α,β-unsaturated aldehyde and a chain conjugated diene compound requires that the reaction be carried out at a high temperature above 100° C. in order to increase the reaction rate since the reaction site of the β-substituted-α,β-unsaturated aldehyde is an internal double bond so that the reactivity is very low. However, under high temperature conditions, a side reaction such as polymerization of the chain conjugated diene compound occurs and therefore it is difficult to practice the reaction in high yields. The rapid increase in reaction rate due to heat generation makes it impossible to control the reaction so that there is a high risk that the runaway of reaction, explosion, etc. will be caused. Therefore, use is made of a catalyst which enables the reaction to be practiced efficiently and at low temperatures.

As for the catalyst for the Diels-Alder reaction between a β-substituted-α,β-unsaturated aldehyde and a chain conjugated diene compound, examples of using aluminum chloride or alkylaluminum halide have been reported. The yields are at most about 50%, which are industrially unsatisfactory (Bull. Chem. Soc., 45, 1553 (1972)).

Furthermore, the examples of using boron trifluoride compounds have been reported (J. Org. Chem. USSR, 7, 2459 (1971), Russian J. Org. Chem., 11, 978 (1975), Russian J. Org. Chem., 21, 1320 (1985)). The replicated experiments of the reaction using boron trifluoride ether complex as a catalyst conducted by the present inventors proved that the reaction of a β-substituted-α,β-unsaturated aldehyde up to a high conversion resulted in an increase in high boiling matters and a considerable decrease in selectivity of the reaction.

The above literature (J. Org. Chem. USSR, 7, 2459 (1971)) shows an example of the reaction between isoprene and crotonaldehyde using a tin (IV) chloride pentahydrate catalyst. This process has the disadvantage in that the reaction rate is low and the catalyst gradually undergoes hydrolysis with the moisture in the catalyst to form hydroxide or oxide of tin, thus causing deactivation or insolubilization of the catalyst.

As stated above, there has been known no technology that enables the Diels-Alder reaction between a β-substituted-α,β-unsaturated aldehyde and a chain conjugated diene compound to proceed in high yields.

Next, as the process of producing a 1,1-cyclohexanedimethanol compound having a substituent group at the 2-position thereof from a 3-cyclohexene-1-carbaldehyde having a substituent group at the 6-position thereof obtained by the Diels-Alder reaction, there is known a process which includes the above-described Cannizzaro reaction between a 3-cyclohexene-1-carbaldehyde having a substituent group at the 6-position thereof and formaldehyde and addition of hydrogen to double bond subsequent thereto. No other production route has been known on a 1,1-cyclohexanedimethanol compound having a substituent group on the 2-position thereof.

As for the production method for a 1,1-cyclohexanedimethanol compound having no substituent group on the 2-position thereof, JP-A-53-65808 (U.S. Pat. No. 4,181,810) discloses a process in which 1-hydroxymethyl-3-cyclohexene-1-carbaldehyde is prepared by the aldol reaction between 3-cyclohexene-1-carbaldehyde and formaldehyde and then reduced. By practicing the aldol reaction between 3-cyclohexene-1-carbaldehyde and formaldehyde using a cation exchange resin as a catalyst according to this process and hydrogenating the aldehyde group of the product using an Ni—Cr—Al catalyst, the carbon-carbon double bond is hydrogenated accessorily to obtain cyclohexane-1,1-dimethanol. However, the yield of cyclohexane-1,1-dimethanol is about 80% of the starting material of the reaction and still unsatisfactory industrially.

Furthermore, the reaction for obtaining 2-substituted-1,3-propanediol by the aldol reaction of an aliphatic aldehyde - hydrogenation reaction is well known for the production process of neopentyl glycol, for example. For example, JP-B-49-11684 discloses a method in which the reaction between isobutyl aldehyde and formaldehyde is carried out using an alkali hydroxide catalyst and then the aldehyde group of the product is hydrogenated using a Cu—Cr catalyst to obtain neopentyl glycol.

DISCLOSURE OF THE INVENTION

1) Object of the Invention

The prior art in which a β-substituted-α,β-unsaturated aldehyde and a chain conjugated diene are used as starting materials to produce a 1,1-cyclohenxanedimethanol having a substituent group at the 2-position thereof in multiple steps has problems in that reaction yield in each step is low, byproducts are generated, and so on and no processes have been known that are satisfactory industrially.

Therefore, an object of the present invention is to provide a process of efficiently producing a 1,1-cyclohexanedimethanol compound having a substituent group at the 2-position thereof, industrially useful as a raw material for polyesters, unsaturated polyesters, alkyds, polyurethanes, epoxy resins, acrylic resins, etc., or as a raw material for functional organic compounds.

Further, another object of the present invention is to provide a process of producing a 3-cyclohexene-1-carbaldehyde compound having a substituent group at the 6-position thereof, which is a productive intermediate for the 1,1-cyclohexanedimethanol compound, a process of producing a 1-hydroxymethyl-3-cyclohexene-1-carbaldehyde compound having a substituent group at least at the 6-position thereof, and novel 1-hydroxymethyl-6-methyl-3-cyclohexene-1-carbaldehyde.

2) Summary of the Invention

The present inventors have intensively investigated the step of producing a 3-cyclohexene-1-carbaldehyde compound having a substituent group at the 6-position thereof by the Diels-Alder reaction between a β-substituted-α,β-unsaturated aldehyde and a chain conjugated diene, the step of producing 1-hydroxymethyl-3-cyclohexene-1-carbaldehyde having a substituent group at the 6-position thereof by the aldol reaction between the carbaldehyde compound above and formaldehyde, and the step of producing the objective 1,1-cyclohexanedimethanol compound having a substituent group at the 2-position thereof by subjecting the 1-hydroxymethyl form to hydrogenation reaction.

As a result, the reason for low yield of the Diels-Alder reaction between a β-substituted-α,β-unsaturated aldehyde and a chain conjugated diene has revealed that:

(1) The reactivity of β-substituted-α,β-unsaturated aldehyde is low;

(2) The aldehyde group of 3-cyclohexene-1-carbaldehyde having a substituent group at the 6-position thereof, the product, is polymerized under acidic conditions to by-produce high boiling compounds; and (3) By-production of high boiling compounds tends to increase where a substance which has high catalytic activity to the Diels-Alder reaction and high Lewis acidity is used or where the reaction is carried out under the conditions under which the concentration of product is high, that is, in a state where the latter part of the reaction proceeds at a high conversion or the amount solvent is small.

The present inventors have investigated catalysts that can solve the above problems. As a result, it has been found that use of an anhydrous tin (IV) halide as a catalyst can solve the above problems to increase the selectivity and yield.

Furthermore, as shown in the following reaction scheme, the aldol reaction between a 3-cyclohexene-1-carbaldehyde having a substituent group at the 6-position thereof and formaldehyde does not proceed in practically acceptable rates with a weakly basic catalyst such as an organic amine catalyst because of poor reactivity of the 3-cyclohexene-1-carbaldehyde having a substituent group at the 6-position thereof so that a strong alkali catalyst such as an alkali metal hydroxide or the like is necessary. However, use of strong alkali catalysts causes a side reaction such as Cannizzaro reaction to occur easily.

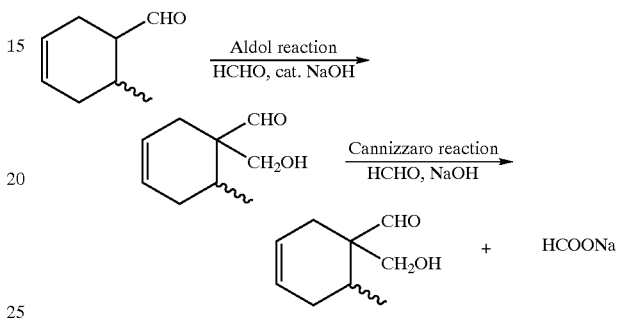

Such a side reaction leads to deactivation or loss of the catalyst due to generation of formic acid salts and therefore a large amount of catalyst must be used in order to increase the conversion of starting materials. However, addition of a large amount of catalyst accelerates the side reaction to produce an increased amount of formic acid salts as by-products, thus deteriorating the quality of product. As a result, there occurs the problem of an increased load in the step of purification.

As a result of intensive investigation, it has now been found that use of an excess amount of 3-cyclohexene-1-carbaldehyde having a substituent group at the 6-position thereof to formaldehyde increases the conversion of formaldehyde to close to about 100% while inhibiting side reactions even when a strong alkali catalyst is used.

Furthermore, it has also been found that hydrogenation can be performed at relatively low temperature and low pressure in good yields in the hydrogenation reaction of a 1-hydroxymethyl-3-cyclohexene-1-carbaldehyde having a substituent group at the 6-position thereof by simultaneously subjecting the aldehyde group and cycloolefin group to the hydrogenation reaction in the presence of catalysts.

The present invention has been achieved based on the above discoveries.

That is, the present invention relates to the following [1] to [14], i.e., a process of producing a 1,1-cyclohexanedimethanol compound having a substituent group at the 2-position thereof of formula (1) from a β-substituted-a,β-unsaturated aldehyde compound of formula (2) and a chain conjugated diene compound of formula (3) as starting materials through intermediary of a 3-cyclohexene-1-carbaldehyde compound having a substituent group at the 6-position of formula (4) and a 1-hydroxymethyl-3-cyclohexene-1-carbaldehyde compound having a substituent group at the 6-position of formula (5), to a process of producing the compound of formula (4), to a process of producing the compound of formula (5), and to novel 1-hydroxymethyl-6-methyl-3-cyclohexene-1-carbaldehyde.

[1] A process of producing 1,1-cyclohexanedimethanol compound having a substituent group at least at the 2-position thereof of formula (1):

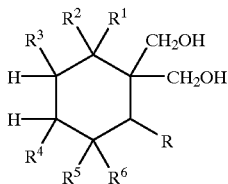

(wherein R and $R^1$ to $R^6$ have the same meanings below), comprising the steps of:
reacting a β-substituted-α,β-unsaturated aldehyde of formula (2):

(wherein R represents an alkyl group having 1 to 4 carbon atoms or a phenyl group) and a chain conjugated diene compound of formula (3):

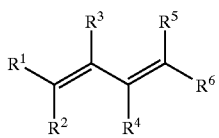

(wherein $R^1$ to $R^6$ independently represent a hydrogen atom or an alkyl group having 1 to 4 carbon atoms) in the presence of an anhydrous tin (IV) halide catalyst to obtain 3-cyclohexene-1-carbaldehyde having a substituent group at least at the 6-position thereof of formula (4):

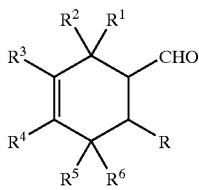

(wherein R and $R^1$ to $R^6$ have the same meanings as defined above), reacting the compound of formula (4) with formaldehyde in the presence of an alkali catalyst to obtain a 1-hydroxymethyl-3-cyclohexene-1-carbaldehyde compound having a substituent group at least at the 6-position thereof of formula (5):

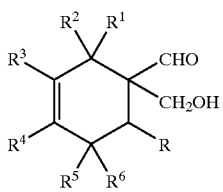

(wherein R and $R^1$ to $R^6$ have the same meanings as defined above), and
subjecting the compound of formula (5) to hydrogenation reaction.

[2] The process of producing the compound of formula (1) as described in [1], wherein the anhydrous tin (IV) halide catalyst is at least one compound selected from anhydrous tin (IV) tetrachloride, anhydrous tin (IV) tetrafluoride, anhydrous tin (IV) tetrabromide, and anhydrous tin (IV) tetraiodide.

[3] The process of producing the compound of formula (1) as described in [1], wherein the compound of formula (2) is crotonaldehyde.

[4] The process of producing the compound of formula (1) as described in [1], wherein the compound of formula (3) is butadiene, isoprene, or 1,3-pentadiene.

[5] The process of producing the compound of formula (1) as described in [1], wherein the alkali catalyst is at least one selected from hydroxides, oxides, carbonates and alkoxides of alkali metals and alkaline earth metals.

[6] The process of producing the compound of formula (1) as described in [5], wherein the alkali catalyst is at least one selected from sodium hydroxide, potassium hydroxide, and calcium hydroxide.

[7] The process of producing the compound of formula (1) as described in [1], wherein the compound of formula (4) is used in an amount of 1.0 to 4.0 moles per mole of formaldehyde.

[8] The process of producing the compound of formula (1) as described in [7], wherein after completion of the reaction between the compound of formula (4) and formaldehyde, unreacted 5 compound of formula (4) is recovered by distillation.

[9] The process of producing the compound of formula (1) as described in [1], further comprising the step of neutralizing the alkali catalyst after completion of the reaction between the compound of formula (4) and formaldehyde.

[10] The process of producing the compound of formula (1) as described in [1], wherein the hydrogenation reaction is carried out at 20 to 100° C.

[11] A process of producing a 1-hydroxymethyl-3-cyclohexene-1-carbaldehyde compound having a substituent group at least at the 6-position thereof of formula (5):

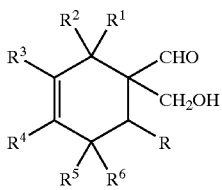

(wherein R and $R^1$ to $R^6$ have the same meanings as defined below), comprising the steps of:
reacting a β-substituted-α,β-unsaturated aldehyde of formula (2):

(wherein R represents an alkyl group having 1 to 4 carbon atoms or a phenyl group) and a chain conjugated diene compound of formula (3):

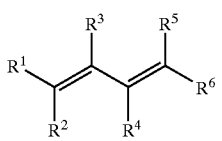

(wherein $R^1$ to $R^6$ independently represent a hydrogen atom or an alkyl group having 1 to 4 carbon atoms) in the presence of an anhydrous tin (IV) halide catalyst to obtain a 3-cyclohexene-1-carbaldehyde having a substituent group at the 6-position thereof of formula (4):

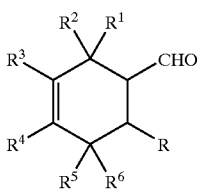

(4)

(wherein R and $R^1$ to $R^6$ have the same meanings as defined above), and reacting the compound of formula (4) with formaldehyde in the presence of an alkali catalyst.

[12] A process of producing a 3-cyclohexene-1-carbaldehyde having a substituent group at the 6-position thereof of formula (4):

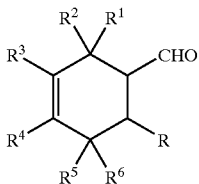

(4)

(wherein R and $R^1$ to $R^6$ have the same meanings as defined below), comprising the step of:

reacting a β-substituted-α,β-unsaturated aldehyde of (2):

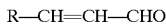

(2)

(wherein R represents an alkyl group having 1 to 4 carbon atoms or a phenyl group) and a chain conjugated diene compound of formula (3):

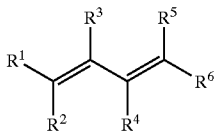

(3)

(wherein $R^1$ to $R^6$ independently represent a hydrogen atom or an alkyl group having 1 to 4 carbon atoms) in the presence of an anhydrous tin (IV) halide catalyst.

[13] A process of producing a compound of formula (1) as described in [1], comprising the steps of:

reacting crotonaldehyde corresponding to formula (2) in which R is a methyl group with butadiene corresponding to formula (3) in which $R^1$ to $R^6$ are each a hydrogen atom in the presence of an anhydrous tin (IV) halide catalyst to obtain 6-methyl-3-cyclohexene-1-carbaldehyde, corresponding to formula (4) in which R is a methyl group and $R^1$ to $R^6$ are each a hydrogen atom, reacting this compound with formaldehyde in the presence of an alkali catalyst to obtain 1-hydroxymethyl-6-methyl-3-cyclohexene-1-carbaldehyde corresponding to formula (5) in which R is a methyl group and $R^1$ to $R^6$ are each a hydrogen atom, and then subjecting this compound to hydrogenation to obtain 2-methyl-1,1-cyclohexanedimethanol corresponding to formula (1) in which R is a methyl group and $R^1$ to $R^6$ are each a hydrogen atom.

[14] 1-Hydroxymethyl-6-methyl-3-cyclohexene-1-carbaldehyde.

DETAILED DESCRIPTION OF THE INVENTION

The following reaction scheme shows a series of reactions according to the present invention from starting materials of a β-substituted-α,β-unsaturated aldehyde of formula (2) and a chain conjugated diene compound of formula (3) to the objective 1,1-cyclohexanedimethanol compound having a substituent group at the 2-position thereof.

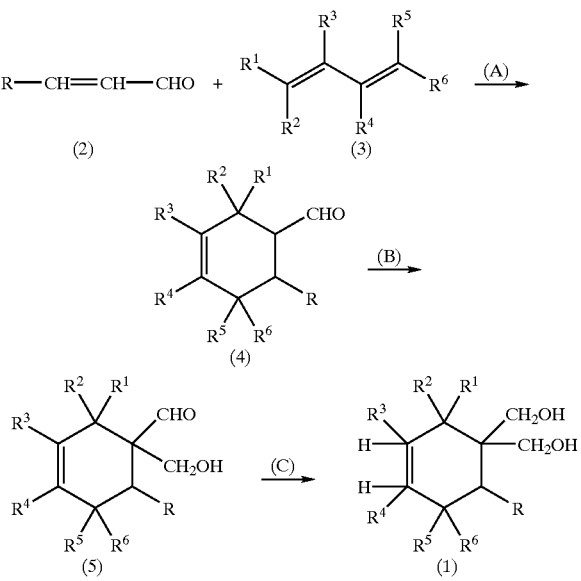

(wherein R and $R^1$ to $R^6$ have the same meanings as defined above).

Hereinafter, the present invention will be described specifically according to the reaction scheme.

1) Diels-Alder Reaction Between a β-Substituted-α,β-unsaturated Aldehyde Compound and a Chain Conjugated Diene Compound (Step A)

The step A is a step in which a β-substituted-α,β-unsaturated aldehyde compound of formula (2) and a chain conjugated diene compound of formula (3) are subjected to Diels-Alder reaction in the presence of an anhydrous tin (IV) halide catalyst.

As the anhydrous tin (IV) halide as a catalyst, anhydrous tin (IV) tetrachloride, anhydrous tin (IV) tetrafluoride, anhydrous tin (IV) tetrabromide, anhydrous tin (IV) tetraiodide, etc. are used.

The use amount of catalyst may vary depending on reaction temperature and concentration of the reaction starting materials and are not particularly limited. From the viewpoints of reaction rate, separation operation for catalyst, economy, etc., however, its preferred range is 0.05% to 20% by mole, more preferably 0.1% to 10% by mole, based on the β-substituted-α,β-unsaturated aldehyde is preferred. If the catalyst amount is below 0.05% by mole, no sufficient reaction result can be obtained while the catalyst amount of above 20% by mole is not preferable since the load of separating catalyst is large and unit of catalyst per production cost is large.

Although the reaction can proceed in the absence of solvents, they may be used, if desired. Any solvent may be used as far as it does not cause side reactions to occur under reaction conditions nor inactivate the catalyst. For example, use can be made of aliphatic hydrocarbons such as butane, isobutane, pentane, hexane, isohexane, heptane, octane, isooctane, decane, cyclopentane, cyclohexane, methylcyclohexane, dimethylcyclohexane, butene, and isobutene, aromatic hydrocarbons such as benzene, toluene, and xylene, halogenated hydrocarbon solvents such as dichloromethane, chloroform, carbon tetrachloride, chloroethane, dichloroethane, trichloroethane, dichloroethylene, trichloroethylene, chlorobenzene, dichlorobenzene, chlorotoluene, and dichlorotoluene. Among these, aromatic hydrocarbons such as benzene, toluene, and xylene are preferred from the viewpoints of the solubility of catalyst, reaction selectivity, etc.

The reaction temperature is in the range of usually 0 to 140° C., preferably 20 to 120° C. Low temperatures of 0° C. or less are impractical since the catalyst activity is insufficient and it takes much time for the reaction. At high temperatures above 140° C., generation of high boiling components increases by side reactions so that the selectivity of the 3-cyclohexene-1-carbaldehyde compound having a substituent group at the 6-position thereof decreases.

The pressure upon reaction is not particularly limited. Usually, the reaction is performed at atmospheric or under pressure. Where a liquefied gas such as butadiene or a highly volatile compound is used as a starting material, the pressurized condition is desirable in order to prevent the volatilization thereof.

When reacted with a catalyst, moisture deteriorates the catalyst activity and the selectivity. Desirably, reaction is carried out in a condition without moisture in the reaction system, if possible. The water content in the reaction system is 2 molar equivalent or less based on the catalyst content, preferably 1 molar equivalent or less.

The mode of reaction is not particularly limited and the reaction may be practiced by a batch-type reaction, a liquid phase continuous reaction or the like.

The order of addition of the reaction components is optional and use can be made of any method from among, for example, a method in which a chain conjugated diene compound is added in the mixture of a β-substituted-α,β-unsaturated aldehyde, a catalyst and a solvent, a method in which a β-substituted-α,β-unsaturated aldehyde and a catalyst are added in a solution of a chain conjugated diene compound, a method in which all of a β-substituted-α,β-unsaturated aldehyde, a chain conjugated diene compound and a catalyst are added in a solvent, and the like.

The charging ratio of the chain conjugated diene compound and the β-substituted-α,p-unsaturated aldehyde compound, starting materials, may be set optionally. However, it is desirable that the reaction be performed at a ratio of 0.5 to 5 molar equivalents, preferably 1 to 4 molar equivalents of the chain conjugated diene compound based on the β-substituted-α,β-unsaturated aldehyde compound. At a ratio of below 0.5 molar equivalent of the chain conjugated diene compound based on the β-substituted-α, β-unsaturated aldehyde compound, no sufficient reaction rate can be obtained. Under the reaction conditions under which the chain conjugated diene compound is present in an amount of more than 5 molar equivalents, the amount of unreacted chain conjugated diene compound increases. This makes separation and purification operations and the like complicated and such conditions are not preferred.

The 3-cyclohexene-1-carbaldehyde having a substituent group at least at the 6-position thereof of formula (4) obtained in the step A is subjected to inactivation and/or separation of the catalyst used in the reaction, to separation of the unreacted chain conjugated diene compound, β-substituted-α,β-unsaturated aldehyde compound, and solvent, and further to isolation of the product, before it can be used in the subsequent step B.

If the catalyst component remains after the reaction, byproducts derived from the product (4) can be generated to decrease yield. Therefore, it is preferred that the catalyst be inactivated or removed as soon as possible.

Separation of the catalyst can be performed by extraction, adsorption, filtration or the like method. In the case of an extraction method, water, diluted hydrochloric acid, diluted sulfuric acid, etc. can be used as an extracting agent. In the case of an adsorption method, activated carbon, silica gel, alumina, magnesia, ion exchange resin or the like can be used as an adsorbent. Further, in the case of a filtration method, for example, the reaction mixture is treated with water or alkali to convert the anhydrous tin (IV) halide, catalyst, to an insoluble compound such as a hydroxide, oxide, or the like, followed by filtration.

Separation of the catalyst can be performed under any of pressurized, normal or reduced pressure condition. Furthermore, the temperature is in the range of 0 to 140° C., preferably 10 to 130° C., more preferably 20 to 120° C.

Isolation of the product (4) may be carried out by distillation, extraction or the like. In particular, a method is preferred in which low boiling compounds such as solvents and unreacted starting materials are distilled off at normal pressure or under reduced pressure before the product (4) can be distilled and isolated. The separation of unreacted starting materials and the solvent and the isolation of the product (4) by distillation may be performed using a plurality of distillation towers under different conditions or one distillation tower depending on the proportions and boiling points of respective components. The distillation conditions are not particularly limited but distillation may be carried out under any of pressurized, normal or reduced pressure condition. The temperature in the distillation step is in the range of 0 to 250° C., preferably 10 to 200° C., and more preferably 20 to 180° C. The solvent or unreacted starting materials recovered by separation operations can be recycled and used by returning them to the reaction system.

The steps of separation of catalysts, separation of unreacted starting materials, and separation of solvents after the reaction may be performed in any order. Furthermore, at least one of the steps of separation of unreacted starting materials, separation of solvents, and isolation of the product (4) may be omitted and crude product containing unreacted starting materials, solvent, or high boiling components can be used in the reaction in the subsequent step.

The substituent group R in the β-substituted- a,β-unsaturated aldehyde compound of formula (2) used as a starting material in the step A is an alkyl group having 1 to 4 carbon atoms or a phenyl group. The alkyl group having 1 to 4 carbon atoms include a methyl group, an ethyl group, a propyl group, an isopropyl group, a butyl group, etc.

The β-substituted-α,β-unsaturated aldehyde compound may be any of E-form, Z-form or an EZ mixture. E-form or EZ mixtures containing a small amount of Z-form that are readily available are preferred.

Specific examples of the β-substituted-α,β-unsaturated aldehyde compound include crotonaldehyde, 2-pentenal, 2-hexenal, 5-methyl-2-hexenal, 2-heptenal, cinnamic aldehyde, etc. Among these, crotonaldehyde is preferred because it is easily available and has a good reactivity.

The chain conjugated diene compound used in the present invention includes those of formula (3) in which the substituent groups $R^1$ to $R^6$ on the conjugated carbon atoms are independently a hydrogen atom or an alkyl group having 1 to 4 carbon atoms.

Specific examples of the chain conjugated diene compound include 1,3-butadiene, isoprene, 1,3-pentadiene, 1,3-hexadiene, 2,4-hexadiene, 2-methyl-1,3-pentadiene, 3-methyl-1,3-pentadiene, 2,3-dimethylbutadiene, 1,3-heptadiene, 2,4-dimethyl-1,3-pentadiene, 1,3-octadiene, etc. but are not limited thereto. Among these dienes, 1,3-butadiene, isoprene, and 1,3-pentadiene are preferred because of their availability, reactivity, and industrial value.

2) Aldol Reaction Between a 3-Cyclohexene-1-carbaldehyde Compound and Formaldehyde (Step B)

The step B is a step for producing a 1-hydroxymethyl-3-cyclohexene-1-carbaldehyde having a substituent group at least at the 6-postion thereof of formula (5) by so-called aldol reaction, in which the compound of formula (4) obtained in the step A and formaldehyde are reacted in the presence of an alkali catalyst.

The formaldehyde used in the reaction may be in any form of aqueous solution, formaldehyde gas or a polymer such as paraformaldehyde.

As the alkali catalyst, any one can be used without limitation as far as it is an alkali compound such as an organic amine compound, alkali metal or alkaline earth metal compound that is used in the aldol reaction between an aliphatic aldehyde and formaldehyde. To obtain good reaction results, strong alkali catalysts are preferred and hydroxides, oxides, carbonates, alkoxides, etc. of alkali metals or alkaline earth metals are used advantageously. More specifically, sodium hydroxide, potassium hydroxide, lithium hydroxide, rubidium hydroxide, cesium hydroxide, magnesium hydroxide, calcium hydroxide, strontium hydroxide, barium hydroxide, sodium oxide, potassium oxide, magnesium oxide, calcium oxide, sodium carbonate, potassium carbonate, lithium carbonate, rubidium carbonate, cesium carbonate, sodium methoxide, sodium ethoxide, sodium propoxide, sodium butoxide, potassium methoxide, potassium ethoxide, potassium propoxide, potassium butoxide, etc. are preferred. Among these, sodium hydroxide, potassium hydroxide, and calcium hydroxide are more preferable.

The use amount of alkali catalyst is 0.001 to 1 molar equivalent, preferably 0.002 to 0.5 molar equivalent, and more preferably 0.005 to 0.3 molar equivalent based on the compound (4), starting material of the reaction.

The charging ratio of the compound (4) and formaldehyde, starting materials of the reaction, may be set such that the molar amount of the compound (4) to formaldehyde is in the range of 0.6 to 5. Preferably, it is set to a molar ratio of above 1.0 based on formaldehyde exceeding the theoretical amount, preferably 1.2 or more, and more preferably 1.5 or more. If the molar ratio of the compound (4) to formaldehyde is small, not only the reaction rate is low but also so-called Cannizzaro reaction, which is a side reaction in which the resulting compound (4) and formaldehyde or formaldehyde molecules with each other are reacted in the presence of an alkali compound to be disproportionated into formic acid and an alcohol. Since alkali formate is produced by the side reaction to consume the alkali catalyst, the rate of aldol reaction is decreased so that it is difficult for the objective aldol reaction to proceed at a high conversion. On the other hand, the upper limit of the molar ratio is preferably 4.0 or less, more preferably 3.0 or less. Under the conditions under which the compound (4) is in a large excess amount, unreacted compound (4) will remain substantially in a large amount so that its separation and recovery is cumbersome.

The reaction of the compound (4) and formaldehyde may be practiced in the presence of an alkali catalyst without solvents. However, it is desirable to carry out the reaction by using a solvent taking into consideration solubilities of formaldehyde and catalyst.

The solvent is not particularly limited as far as it does not react with the product or catalyst. Specific examples thereof include alcohols such as methanol, ethanol, propanol, isopropanol, butanol, and ethylene glycol, ethers such as tetrahydrofuran, 1,4-dioxane, and 1,2-dimethoxyethane, ether alcohols such as ethylene glycol monomethyl ether, ethylene glycol monoethyl ether, and diethylene glycol, and the like. Among these, alcohol solvents are used advantageously from the viewpoints of solubility. In particular, methanol and ethanol are preferred.

The reaction temperature is 0 to 140° C., preferably 10 to 100° C., and more preferably 10 to 80° C. If the reaction temperature is low, a decrease in reaction rates results. If the reaction temperature is high, for example, decomposition of the product occurs, thus causing a decrease in yield.

The product (5) is usually subjected to the step of removing the solvent, water, unreacted starting materials and catalyst from the reaction mixture before it can be supplied to the subsequent step C. Separation of these components can be performed by distillation, extraction, etc.

In the separation and purification after the reaction, it is desirable that the alkali catalyst be neutralized as soon as the reaction is completed. If the alkali component remains, the product (5) will be decomposed or condensed (Tishchenko reaction) and the yield may be decreased. As the acid used for neutralization, use can be made of hydrochloric acid, hydrobromic acid, sulfuric acid, nitric acid, phosphoric acid, formic acid, acetic acid, boric acid, p-toluenesulfonic acid, and dilutions thereof, acidic ion exchange resins, etc. In particular, hydrochloric acid, sulfuric acid, phosphoric acid, and formic acid are used advantageously.

The step of separating and purifying the product (5) is preferably performed at a relatively low temperature in order to prevent the decomposition of the product. The temperature for the treatment such as distillation or extraction is preferably 140° C. or less, more preferably 120° C. or less.

The separation step may be omitted partly or entirely as far as the solvent, water, catalyst or the like carried over to the subsequent step C will not adversely affect the catalyst activity or selectivity of the hydrogenation reaction.

Among the compounds of formula (5) obtained in the present step, 1-hydroxymethyl-6-methyl-3-cyclohexene-1-carbaldehyde of the following formula:

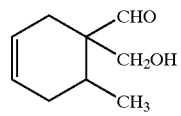

which corresponds to formula (5) in which R is a methyl group and $R^1$ to $R^6$ are each a hydrogen atom, is a new compound.

3) Hydrogenation Reaction of a 1-Hydroxymethyl-3-cyclohexene-1-carbaldehyde Compound (Step C)

The step C is the one in which a 1-hydroxymethyl-3-cyclohexene-1-carbaldehyde having a substituent group at least at the 6-position thereof of formula (5) obtained in the step B is subjected to hydrogenation reaction in the presence of a catalyst to produce a 1,1-cyclohexanedimethanol having a substituent group at least at the 2-position thereof of formula (1).

The hydrogenation reaction is carried out at a reaction temperature in the range of 0 to 160° C., preferably 10 to 130° C., and more preferably 20 to 100° C. If the reaction temperature is too high, the starting material compound (5) may be thermally decomposed. On the contrary, if the reaction temperature is too low, the reaction rate will be decreased. The reaction is carried out at a hydrogen pressure in the range of 0.1 to 50 MPa, preferably 0.2 to 40 MPa, and more preferably 0.3 to 30 MPa.

As the catalyst, either homogeneous or heterogeneous catalysts may be used. From the viewpoint of ease of separation, heterogeneous catalysts are preferred.

The heterogeneous catalyst that can be used include those that partly or entirely comprise at least one of nickel, palladium, platinum, copper, silver, gold, cobalt, rhodium, iridium, iron, ruthenium, and osmium. The catalysts may further contain aluminum, boron, magnesium, barium, zinc, chromium, molybdenum, tungsten, manganese, etc. Among these, those catalysts that partly or entirely comprise at least one of nickel, palladium, platinum, cobalt, ruthenium, and copper are more preferable. Specific examples of hydrogenation catalyst include reduced Ni, sponge Ni (Ni—Al metal, trade name: Raney nickel), Ni—Cr, Ni—Cr—Al, Ni—Cr—Mo, Ni—Cu, Ni—Cu—Mn, Ni—Cu—P, sponge Cu, Cu—Cr, Cu—Cr—Ba, Cu—Zn, Cu—Zn—Zr, Pd—Ru, $PtO_2$, Pt—Ru, Pt—Ru—W. However, the present invention is not limited thereto.

As the catalyst, the metal component may be used alone or the one carried on a suitable carrier may be used. Furthermore, two or more catalysts may be used as admixture.

The hydrogenation reaction using heterogeneous catalyst may be carried out in any form such as suspended bed, fixed bed reaction etc. depending on the catalyst used. Upon hydrogenating both of the aldehyde group and olefinic double bond of. the compound (5), the reaction may be carried out as a multi-stage hydrogenation reaction by dividing the reactor into two or more parts that are under different reaction conditions and use different catalysts.

It is possible to carry out the hydrogenation reaction by allowing the compound (5) as it is in a molten state to contact the catalyst under hydrogen atmosphere. However, it is preferred to use a solvent and perform the reaction in a solution state.

The solvent used in the hydrogenation reaction includes alcohol solvents such as methanol, ethanol, propanol, isopropanol, and butanol, ether solvents such as tetrahydrofuran, dioxane, and 1,2-dimethoxyethane, ether alcohol solvents such as ethylene glycol monomethyl ether, ethylene glycol monoethyl ether, and diethylene glycol, hydrocarbon solvents such as hexane, benzene, toluene, and xylene, mixtures of two or more these, and so on. Among these, alcohol solvents, particularly methanol and ethanol solvents are used preferably.

In the case of hydrogenation reaction using heterogeneous catalysts, the reaction mixture after the reaction may optionally be subjected to filtration, decantation or the like operation to remove the hydrogenation catalyst and then the solvent is distilled off under normal or reduced pressure to obtain a crude product of 1,1-cyclohexanedimethanol having a substituent group at the 2-position thereof (1), the objective substance. The distilled off hydrogenation reaction solvent can be used again as a solvent for hydrogenation reaction of the present invention.

Crude products can be purified by distillation, recrystallization or the like operation. Recrystallization solvent includes hydrocarbons such as hexane, octane, cyclohexane, benzene, toluene, and xylene, halogenated hydrocarbons such as dicloromethane, chloroform, and 1,2-dichloroethane, alcohols such as methanol, ethanol, propanol, isopropanol, and butanol, ketones such as acetone and methyl ethyl ketone, esters such as ethyl acetate, propyl acetate, and butyl acetate, ethers such as diisopropyl ether, 1,2-dimethoxyethane, tetrahydrofuran, and 1,4-dioxane, water, and so on. As a recrystallization solvent, mixtures of two or more of the above can be used.

BEST MODE FOR CARRYING OUT THE INVENTION

Hereinafter, the present invention will be described in detail by examples and comparative examples. However, the present invention is not limited to the examples. Measurements by gas chromatography (GC), $^1$H-NMR, $^{13}$C-NMR, and FT-IR were carried out under the following conditions.

1) GC Analysis

Analyzer: Gas chromatograph GC-9A, manufactured by Shimadzu Corporation

Carrier gas: He, 1 ml/minute, split ratio: 1/50

Detector: FID

Column: NEUTRABOND-1 (0.25 mm$\phi$×60m, liquid film thickness:1.5 $\mu$m), manufactured by G.L. Science, Ltd.

Column temperature: 150° C. (8 minutes)→32° C./minute→200° C. (30 minutes)

2) $^1$H-NMR, $^{13}$C-NMR

Measuring apparatus: JNM-EX 400 Model (400 MHz) spectrometer, manufactured by NIPPON DENSHI, Ltd. (English appellation: JEOL, Ltd.).

Solvent: $CDCl_3$

Internal standard substance: Tetramethylsilane

3) FT-IR

Measurement apparatus: Spectrum GX Spectrometer, manufactured by Perkin-Elmer

Measuring method: KBr liquid film method

EXAMPLE 1

Diels-Alder Reaction Between Crotonaldehyde and Butadiene Using an Anhydrous Tin (IV) Chloride Catalyst In a 1-L autoclave equipped with a stirrer were charged 113.9 g (1.63 mol) of crotonaldehyde and 153 ml of benzene. The contents were purged with nitrogen by repeating the operation of pressurization to a nitrogen pressure of 0.5 MPa and decompression four times. 8.28 g (31.8 mmol) of anhydrous tin (IV) chloride was added using a syringe and again the operation of pressurization to a nitrogen pressure of 0.5 MPa and decompression was repeated four times to establish a nitrogen atmosphere. Thereafter, the inner temperature was elevated to 60° C. To the solution was injected 87.9 g (1.63 mol) of butadiene and the system was pressurized to 0.5 MPa with nitrogen gas.

While keeping the reaction temperature as it is at 60° C., the reaction was allowed to proceed for 6 hours with stirring.

After the reaction, the reaction mixture was cooled to room temperature and a portion of the reaction mixture was collected. The reaction mixture was analyzed by gas chromatography (GC) analysis to analyze each component. As a result, crotonaldehyde had a conversion of 90.2% and 6-methyl-3-cyclohexene-1-carbaldehyde had a selectivity of 85.5% and a yield of 77.2%.

EXAMPLE 2

Diels-Alder Reaction Between Crotonaldehyde and Butadiene Using an Anhydrous Tin (IV) Chloride Catalyst Reaction was performed at 60° C. in the same manner as in Example 1 except that 87.1 g (1.24 mol) of crotonaldehyde, 188 ml of benzene, 6.47 g (24.8mmol) of anhydrous tin (IV) chloride, and 86.5 g (1.60 mol) of butadiene were used.

After 7 hours' reaction, GC analysis of the reaction mixture revealed that crotonaldehyde had a conversion of 97.2% and 6-methyl-3-cyclohexene-1-carbaldehyde had a selectivity of 91.5% and a yield of 89.0%.

EXAMPLE 3

Diels-Alder Reaction Between Crotonaldehyde and Butadiene Using an Anhydrous Tin (IV) Chloride Catalyst and Purification In a 1-L autoclave equipped with a stirrer were charged 60.86 g (0.868 mol) of crotonaldehyde and 188 ml of benzene. The contents were purged with nitrogen by repeating the operation of pressurization at a nitrogen pressure of 0.5 MPa and decompression four times. Thereafter, 0.675 g (2.59 mmol) of anhydrous tin (IV) chloride was added using a syringe and again the operation of pressurization at a nitrogen pressure of 0.5 MPa and decompression was repeated four times to establish a nitrogen atmosphere. The solution was heated and when the reaction mixture reached to about 40° C., 87.9 g (1.63 mol) of butadiene was injected and the inside of the system was pressurized to 0.5 MPa with nitrogen gas. Thereafter, heating was continued to elevate the inner temperature to 90° C.

While keeping the reaction temperature as it is at a constant temperature of 90° C., the reaction was continued with stirring. At the onset of the reaction, the reaction pressure showed at most 0.68 MPa but thereafter decreased to 0.60 MPa after 7 hours.

After 7 hours' reaction, the reaction mixture was cooled to room temperature and a portion of the reaction mixture was collected. The reaction mixture was analyzed by gas chromatography (GC) analysis to analyze each component. As a result, crotonaldehyde had a conversion of 96.6% and 6-methyl-3-cyclohexene-1-carbaldehyde had a selectivity of 91.0% and a yield of 87.9%.

To the obtained reaction mixture was added 50 ml of 1 mol/liter hydrochloric acid and the mixture was stirred for 10 minutes to extract the anhydrous tin (IV) chloride. After standing it for 30 minutes, the water layer was separated and removed. Further, 50 ml of water was added and the procedure of stirring for 10 minutes, standing for 30 minutes and separation of water layer was repeated 3 times to wash the organic layer.

The obtained organic layer was transferred into a 500 ml flask equipped with a 20-cm Vigreaux distilling column and the contents were heated on an oil bath while stirring by a magnetic stirrer while slowly elevating the inner temperature to distilling off low boiling compounds, i.e., butadiene, benzene and crotonaldehyde. The inner temperature was elevated finally to 115° C. to distill low boiling components off. Thereafter, the obtained concentrate was transferred into a 200 ml flask equipped with a 20-cm Vigreaux distilling column and distillation under reduced pressure was practiced to obtain 87.4 g of a fraction of 6.7 kPa at 102 to 103° C. as a main fraction. GC analysis of the fraction revealed that 6-methyl-3-cyclohexene-1-carbaldehyde in the fraction was in an amount of 80.9 g.

EXAMPLE 4

Diels-Alder Reaction Between Crotonaldehyde and Isoprene Using an Anhydrous Tin (IV) Chloride Catalyst The reaction was practiced at 60° C. in the same manner as in Example 1 except that a 120-ml autoclave was used and 17.5 g (0.25 mol), 30 ml of toluene, 1.25 g (5.0 mmol) of anhydrous tin (IV) chloride, and 17.0 g (0.25 mol) of isoprene were used.

After 7 hours' reaction, GC analysis of the reaction mixture revealed that crotonaldehyde had a conversion of 97.2% and 4,6-dimethyl-3-cyclohexene-1-carbaldehyde had a selectivity of 88.0% and a yield of 85.5%.

EXAMPLE 5

Diels-Alder Reaction Between Crotonaldehyde and Butadiene Using an Anhydrous Tin (IV) Bromide Catalyst The reaction was practiced at 60° C. in the same manner as in Example 1 except that a 120-ml autoclave was used and 17.5 g (0.25 mol), 30 ml of toluene, 2.19 g (5.0 mmol) of anhydrous tin (IV) bromide, and 13.5 g (0.25 mol) of butadiene were used.

After 7 hours' reaction, GC analysis of the reaction mixture revealed that crotonaldehyde had a conversion of 89.2% and 6-methyl-3-cyclohexene-1-carbaldehyde had a selectivity of 85.0% and a yield of 79.8%.

COMPARATIVE EXAMPLE 1

Diels-Alder Reaction Between Crotonaldehyde and Butadiene Using a Boron Trifluoride Ether Complex Catalyst The reaction was practiced at 60° C. in the same manner as in Example 1 except that 162 g (2.31 mol) of crotonaldehyde, 250 ml of toluene, 126.4 g (2.34 mol) of butadiene and 6.40 g (45.1 mmol) of boron trifluoride ether complex as a catalyst were used.

After 7 hours' reaction, GC analysis of the reaction mixture revealed that crotonaldehyde had a conversion of 79.1% and 6-methyl-3-cyclohexene-1-carbaldehyde had a selectivity of 65.2 % and a yield of 52.4%.

COMPARATIVE EXAMPLE 2

Diels-Alder Reaction Between Crotonaldehyde and Butadiene Using a Tin (IV) chloride Pentahydrate Catalyst The reaction was practiced at 60° C. in the same manner as in Example 1 except that 112 g (1.59 mol) of crotonaldehyde, 172 ml of benzene, 86.0 g (1.59 mol) of butadiene and 11.2 g (31.8 mmol) of tin (IV) chloride pentahydrate as a catalyst were used.

After 7 hours' reaction, GC analysis of the reaction mixture revealed that crotonaldehyde had a conversion of 46.0% and 6-methyl-3-cyclohexene-1-carbaldehyde had a selectivity of 94.0 % and a yield of 43.2%.

Table 1 shows the results of Examples 1 to 5 and Comparative Examples 1 and 2. It will be understood that the process of the present invention increases the yield of the objective products.

TABLE 1

|  | Starting Material 1 (A) | Starting Material 2 (B) | B/A (molar ratio) | Catalyst | Conversion (%) | Selectivity (%) | Yield (%) |
| --- | --- | --- | --- | --- | --- | --- | --- |
| Example 1 | CALD | BD | 1.00 | $SnCl_4$ | 90.2 | 85.5 | 77.2 |
| Example 2 | CALD | BD | 1.29 | $SnCl_4$ | 97.2 | 91.5 | 89.0 |
| Example 3 | CALD | BD | 1.88 | $SnCl_4$ | 96.6 | 91.0 | 87.9 |
| Example 4 | CALD | IP | 1.00 | $SnCl_4$ | 97.2 | 88.0 | 85.5 |
| Example 5 | CALD | BD | 1.00 | $SnCl_4$ | 89.2 | 85.0 | 79.8 |
| Comparative Example 1 | CALD | BD | 1.00 | $BF_3$-ether | 79.1 | 65.2 | 52.4 |
| Comparative Example 2 | CALD | BD | 1.00 | $SnCl_4 \cdot 5H_2O$ | 46.0 | 94.0 | 43.2 |

CALD: Crotonaldehyde, BD: Butadiene, IP: Isoprene
Conversion and yield: Based on CALD

EXAMPLE 6

Diels-Alder Reaction of 6-Methyl-3-cyclohexne-1-carbaldehyde

In a 200-ml flask containing a magnetic stirrer were charged 62.21 g (0.5004 mol) of 6-methyl-3-cyclohexne-1-carbaldehyde, 20.34 g (formaldehyde: 0.2505 mol) of an aqueous about 37 mass % formaldehyde solution, and 38.83 g of methanol and the mixture was stirred at room temperature to make the system homogeneous. Further, while stirring at room temperature, 1.67 g (NaOH: 20 mmol) of an aqueous 48 mass % of sodium hydroxide solution was added. Then, the transparent reaction mixture turned dense yellow and further black. After 1 hour from the addition of an aqueous sodium hydroxide solution, the reaction mixture was neutralized with an aqueous 10% sulfuric acid solution to adjust pH 6. Then, the reaction mixture changed in color from black to pale yellow.

Sampling a portion of the reaction mixture and its GC analysis revealed that 6-methyl-3-cyclohexene-1-carbaldehyde had a conversion of 53.0%, 6-methyl-1-hydroxylmethyl-3-cyclohexene-1-carbaldehyde had a yield of 53.0% and thus the 6-methyl-1-hydroxylmethyl-3-cyclohexene-1-carbaldehyde had a selectivity of 99% or more. On the GC chromatogram, the peak of formaldehyde disappeared.

Then, the neutralized liquid was heated on an oil bath at 100° C. and distilled at normal pressure to distill off methanol to obtain 41.22 g of a fraction having a distillation temperature of 69 to 78° C. GC analysis of the methanol fraction indicated that it contained 1.45 g of 6-methyl-3-cyclohexene-1-carbaldehyde. After the distillation of methanol, the residual liquid was separated into two layers. The liquid was separated into an organic layer (72.19 g) and an aqueous layer (9.50 g) using a separating funnel and both the organic layer and the aqueous layer were GC analyzed, respectively. The organic layer contained 26.69 g of 6-methyl-3-cyclohexene-1-carbaldehyde, 36.59 g of 6-methyl-1-hydroxymethyl-3-cyclohexene-1-carbaldehyde, and 0.38 g of 6-methyl-3-cyclohexene-1,1-dimethanol while the aqueous layer contained 0.13 g of 6-methyl-1-hydroxymethyl-3-cyclohexene-1-carbaldehyde, trace amounts of 6-methyl-3-cyclohexene-1-carbaldehyde and of 6-methyl-3-cyclohexene-1,1-dimethanol, respectively.

Then, the organic layer was transferred into a 100-ml flask and distillation under reduced pressure was carried out to recover 6-methyl-3-cyclohexene-1-carbaldehyde, the starting material. The fraction obtained by distilling off at an oil bath temperature of 100° C. and at a pressure of from 20 kPa to 6.7 kPa was named fraction-1 and the fraction obtained from 65° C. at a pressure of 1.7 kPa to 50° C. at a pressure of 0.27 kPa by distilling off at an oil bath temperature of 100° C. was named fraction-2. The obtained fraction-1 weighed 6.37 g and its GC analysis revealed that it contained 1.11 g of 6-methyl-3-cyclohexene-1-carbaldehyde. The fraction-2 weighed 22.96 g and its GC analysis revealed that it contained 22.65 g of 6-methyl-3-cyclohexene-1-carbaldehyde and 0.31 g of 6-methyl-1-hydroxymethyl-3-cyclohexene-1-carbaldehyde.

The residue after the distillation weighed 39.76 g and its GC analysis revealed that it contained 34.90 g of 6-methyl-1-hydroxymethyl-3-cyclohexene-1-carbaldehyde, 0.33 g of 6-methyl-3-cyclohexene-1-carbaldehyde, and 0.38 g of 6-methyl-3-cyclohexene-1,1-dimethanol, respectively.

The recovered 6-methyl-3-cyclohexene-1-carbaldehyde weighed 25.51 g in total. This means that 40.5% of the originally charged 6-methyl-3-cyclohexene-1-carbaldehyde was recovered. The yield of 6-methyl-1-hydroxymethyl-3-cyclohexene-1-carbaldehyde in the residue was 45.2% of the originally charged 6-methyl-3-cyclohexene-1-carbaldehyde. This corresponds to a theoretical yield of 90.4%.

Further, the residue obtained above was distilled under reduced pressure to obtain a fraction of having a boiling point of 84° C. (0.05 kPa) to 74° C. (0.04 kPa). GC analysis of the obtained fraction revealed that the purity of 6-methyl-1-hydroxymethyl-3-cyclohexene-1-carbaldehyde was 96.8 mass %.

The $^1$H-NMR, $^{13}$C-NMR, and IR (infrared absorption) spectral data of the obtained 6-methyl-1-hydroxymethyl-3-cyclohexene-1-carbaldehyde are as shown below.

$^1$H-NMR Spectrum: 0.8–1.0 ppm (3H, cy-$CH_3$); 1.6–2.6 ppm (5H, cy-H); 3.5–3.9 ppm (2H, —$CH_2O$—); 5.4–5.8 ppm (2H, —CH=CH—); 9.69, 9.56 ppm (1H, —CHO).

$^{13}$C-NMR Spectrum: 14.0–15.8 ppm (—$CH_3$); 25.0–26.0, 28.1–30.3, 50.6, 52.5, 52.7 ppm (C(cy)); 61.8, 63.6–68.3 ppm (—$CH_2OH$); 123.1–125.9 ppm (—C=C—); 207.6, 207.7 ppm (—CHO).

IR Spectrum: 3430 cm$^{-1}$ (vO—H); 3027, 2966, 2900, 2845 cm$^{-1}$ (vC—H); 1723 cm$^{-1}$ (vC=O); 1654 cm$^{-1}$ (vC=C).

EXAMPLE 7

Hydrogenation Reaction of 6-Methyl-1-hydroxymethyl-3-cyclohexene-1-carbaldehyde

In a 120-ml stainless steel autoclave equipped with a stirrer (manufactured by Taiatsu Glass Co.) was charged 5 g of a starting material (93.3 mass % of 6-methyl-1- hydroxymethyl-3-cyclohexene-1-carbaldehyde, 5.9 mass % of 6-methyl-3-cyclohexene-1-carbaldehyde, and 0.8 mass % of 6-methyl-3-cyclohexene-1,1-dimethanol) dissolved in 45 g of methanol.

Then, Raney nickel was developed by the method described in the literature (Bull. Chem. Soc. Jpn., 32, 61 (1959)) to prepare a hydrogenation catalyst (T-4 sponge nickel catalyst). More specifically, a vessel containing 1.1 g of Raney)nickel (manufactured by Wako Pure Chemical Industry Co., Ltd., 50% Ni content) to which 5 ml of distilled water was added was dipped in a warm bath at 50° C. and while stirring sufficiently, 0.2 ml of an aqueous 20 mass % sodium hydroxide solution was added. In about 30 minutes, abruptly hydrogen was generated. After the generation of hydrogen substantially ceased, the stirring was continued for further 30 minutes. Then, 3 ml of an aqueous 40 mass % sodium hydroxide solution was added and the mixture was stirred at 50° C. for 1 hour. Thereafter, turbid supernatant was removed by a decantation method. Thereafter, the resulting catalyst was washed with 8 ml of water that had been boiled, deaerated and cooled to 50° C. four times. Further, the catalyst was washed with 8 ml of methanol three times. Thus, a hydrogenation reaction catalyst (T-4 sponge nickel catalyst) was obtained.

The hydrogenation catalyst was flown together with a small amount of methanol into the autoclave in which a starting material solution was charged. The autoclave was tightly closed and the operation of elevating the pressure to a pressure of 0.5 MPaG (here G means gauge pressure and a differential pressure from the atmospheric pressure is expressed with MPaG) and decompression was repeated five times to replace the atmosphere inside the autoclave by nitrogen. Subsequently, the operation of elevating the pressure to 0.5 MPaG with hydrogen and decompression was repeated 3 times to replace the atmosphere in the autoclave by hydrogen, and finally the pressure was elevated to 0.5 MPaG with hydrogen. Thereafter, stirring was started at 800 rpm to initiate the reaction. The reaction was carried out by supplying hydrogen from a pressure accumulator equipped with a pressure gauge so that the hydrogen pressure was kept at 0.5 MPaG. After stirring at room temperature for 1 hour, the temperature was elevated to 50° C. in 15 minutes and stirring was continued at 50° C. for 4 hours. Thereafter, the stirring was stopped, the reaction system was decompressed and the operation of elevating the pressure to 0.5 MPaG with nitrogen and decompression was repeated 5 times to replace the atmosphere inside the autoclave by nitrogen. The autoclave was opened and an aliquot of the supernatant of the contents was taken out. GC analysis of the supernatant revealed that it contained 90.9 mass % of 2-methyl-1,1-cyclohexanedimethanol, 2.8 mass % of 6-methyl-1-hydroxymethyl-3-cyclohexene-1-carbaldehyde, 1.6 mass % of 2-methyl-1-hydroxymethyl cyclohexane-1-carbaldehyde, 2.6 mass % of 2-methyl-1-cyclohexanemethanol, and 1.7 mass % of 6-methyl-3-cyclohexene-1-carbaldehyde.

The results indicated that 6-methyl-1-hydroxymethyl-3-cyclohexene-1-carbaldehyde had a conversion of 97.0%, 2-methylcyclohexanedimethanol had a selectivity of 98.2% and a yield of 95.2%. Further, 6-methyl-1-hydroxymethyl-3-cyclohexene-1-carbaldehyde had a hydrogenation ratio of aldehyde group of 98% and hydrogenation ratio of cycloolefin double bond of 99% or more.

INDUSTRIAL APPLICABILITY

According to the present invention, 1,1-cyclohexanedimethanol compounds having a substituent group at least at the 2-position thereof can be produced from β-substituted-α,β-unsaturated aldehydes and chain conjugated diene compounds in improved yields. 1,1-Cyclohexanedimethanol compounds having a substituent group at least at the 2-position thereof and productive intermediates thereof obtained by the present invention are useful in industry as a raw material for polyesters, unsaturated polyesters, alkyds, polyurethanes, epoxy resins, acrylic resins, etc. and as intermediates for organic synthesis.

What is claimed is:

1. A process of producing a 1,1-cyclohexanedimethanol compound having a substituent group at least at the 2-position thereof of formula (1):

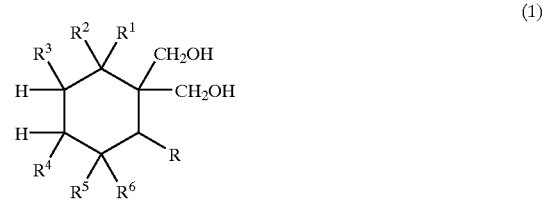

(1)

(wherein R and $R^1$ to $R^6$ have the same meanings below), comprising the steps of:

reacting a β-substituted-α,β-unsaturated aldehyde of formula (2):

R—CH=CH—CHO (2)

(wherein R represents an alkyl group having 1 to 4 carbon atoms or a phenyl group) and a chain conjugated diene compound of formula (3):

(3)

(wherein $R^1$ to $R^6$ independently represent a hydrogen atom or an alkyl group having 1 to 4 carbon atoms) in the presence of an anhydrous tin (IV) halide catalyst to obtain a 3-cyclohexene-1-carbaldehyde having a substituent group at least at the 6-position thereof of formula (4):

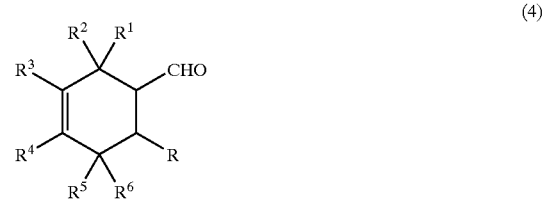

(4)

(wherein R and $R^1$ to $R^6$ have the same meanings as defined above), reacting the compound of formula (4) with formaldehyde in the presence of an alkali catalyst to obtain a 1-hydroxymethyl-3-cyclohexene-1-carbaldehyde compound having a substituent group at least at the 6-position thereof of formula (5):

(5)

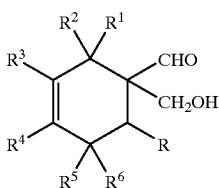

(wherein R and R¹ to R⁶ have the same meanings as defined above), and subjecting the compound of formula (5) to hydrogenation reaction.

2. The process of producing the compound of formula (1) as claimed in claim 1, wherein the anhydrous tin (IV) halide catalyst is at least one compound selected from anhydrous tin (IV) tetrachloride, anhydrous tin (IV) tetrafluoride, anhydrous tin (IV) tetrabromide, and anhydrous tin (IV) tetraiodide.

3. The process of producing the compound of formula (1) as claimed in claim 1, wherein the compound of formula (2) is crotonaldehyde.

4. The process of producing the compound of formula (1) as claimed in claim 1, wherein the compound of formula (3) is butadiene, isoprene, or 1,3-pentadiene.

5. The process of producing the compound of formula (1) as claimed in claim 1, wherein the alkali catalyst is at least one selected from hydroxides, oxides, carbonates and alkoxides of alkali metals and alkaline earth metals.

6. The process of producing the compound of formula (1) as claimed in claim 5, wherein the alkali catalyst is at least one selected from sodium hydroxide, potassium hydroxide, and calcium hydroxide.

7. The process of producing the compound of formula (1) as claimed in claim 1, wherein the compound of formula (4) is used in an amount of 1.0 to 4.0 moles per mole of formaldehyde.

8. The process of producing the compound of formula (1) as claimed in claim 7, wherein after completion of the reaction between the compound of formula (4) and formaldehyde, unreacted compound of formula (4) is recovered by distillation.

9. The process of producing the compound of formula (1) as claimed in claim 1, further comprising the step of neutralizing the alkali catalyst after completion of the reaction between the compound of formula (4) and formaldehyde.

10. The process of producing the compound of formula (1) as claimed in claim 1, wherein the hydrogenation reaction is carried out at 20 to 100° C.

11. A process of producing a 1-hydroxymethyl-3-cyclohexene-1-carbaldehyde compound having a substituent group at least at the 6-position thereof of formula (5):

(5)

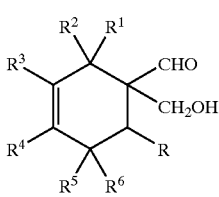

(wherein R and R¹ to R⁶ have the same meanings as defined below), comprising the steps of:

reacting a β-substituted-α,β-unsaturated aldehyde of formula (2):

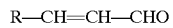

R—CH=CH—CHO (2)

(wherein R represents an alkyl group having 1 to 4 carbon atoms or a phenyl group) and a chain conjugated diene compound of formula (3):

(3)

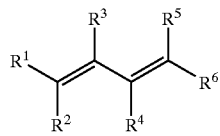

(wherein R¹ to R⁶ independently represent a hydrogen atom or an alkyl group having 1 to 4 carbon atoms) in the presence of an anhydrous tin (IV) halide catalyst to obtain 3-cyclohexene-1-carbaldehyde having a substituent group at the 6-position thereof of formula (4):

(4)

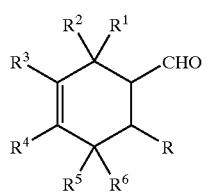

(wherein R and R¹ to R⁶ have the same meanings as defined above), and reacting the compound of formula (4) with formaldehyde in the presence of an alkali catalyst.

12. A process of producing a 3-cyclohexene-1-carbaldehyde having a substituent group at the 6-position thereof of formula (4):

(4)

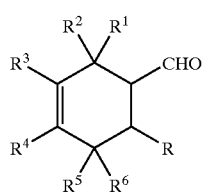

(wherein R and R¹ to R⁶ have the same meanings as defined below), comprising the step of:

reacting a β-substituted-α,β-unsaturated aldehyde of formula (2)

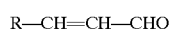

R—CH=CH—CHO (2)

(wherein R represents an alkyl group having 1 to 4 carbon atoms or a phenyl group) and a chain conjugated diene compound of formula (3):

(3)

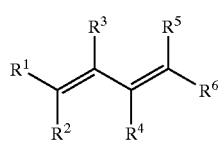

(wherein R¹ to R⁶ independently represent a hydrogen atom or an alkyl group having 1 to 4 carbon atoms) in the presence of an anhydrous tin (IV) halide catalyst.

13. A process of producing a compound of formula (1) as claimed in claim 1, comprising the steps of:

reacting crotonaldehyde corresponding to formula (2) in which R is a methyl group with butadiene corresponding to formula (3) in which $R^1$ to $R^6$ are each a hydrogen atom in the presence of an anhydrous tin (IV) halide catalyst to obtain 6-methyl-3-cyclohexene-1-carbaldehyde, corresponding to formula (4) in which R is a methyl group and $R^1$ to $R^6$ are each a hydrogen atom, reacting this compound with formaldehyde in the presence of an alkali catalyst to obtain 1-hydroxymethyl-6-methyl-3-cyclohexene-1-carbaldehyde corresponding to formula (5) in which R is a methyl group and $R^1$ to $R^6$ are each a hydrogen atom, and then subjecting this compound to hydrogenation to obtain 2-methyl-1,1-cyclohexanedimethanol corresponding to formula (1) in which R is a methyl group and $R^1$ to $R^6$ are each a hydrogen atom.

14. 1-Hydroxymethyl-6-methyl-3-cyclohexene-1-carbaldehyde.

* * * * *